(12) United States Patent
Ibrahim et al.

(10) Patent No.: US 10,945,767 B2
(45) Date of Patent: Mar. 16, 2021

(54) SYSTEMS, ASSEMBLIES AND METHODS FOR SPINAL DEROTATION

(71) Applicant: SpineCraft, LLC, Westmont, IL (US)

(72) Inventors: Kamal Ibrahim, Chicago, IL (US); Wagdy W. Asaad, Burr Ridge, IL (US); Thibaut Guffroy, Westmont, IL (US)

(73) Assignee: SpineCraft, LLC, Westmont, IL (US)

( * ) Notice: Subject to any disclaimer, the term of this patent is extended or adjusted under 35 U.S.C. 154(b) by 247 days.

(21) Appl. No.: 16/248,492

(22) Filed: Jan. 15, 2019

(65) Prior Publication Data

US 2019/0142475 A1 May 16, 2019

Related U.S. Application Data

(60) Continuation of application No. 15/822,047, filed on Nov. 24, 2017, now Pat. No. 10,213,232, which is a
(Continued)

(51) Int. Cl.
*A61B 17/70* (2006.01)
*A61B 17/86* (2006.01)
(Continued)

(52) U.S. Cl.
CPC .......... *A61B 17/7032* (2013.01); *A61B 17/70* (2013.01); *A61B 17/7002* (2013.01);
(Continued)

(58) Field of Classification Search
USPC ....................................... 606/250, 279, 86 A
See application file for complete search history.

(56) References Cited

U.S. PATENT DOCUMENTS

| 4,409,968 A | 10/1983 | Drummond |
| 4,505,268 A | 3/1985 | Sgandurra |

(Continued)

OTHER PUBLICATIONS

APEX Spine System Vertebral Body Derotation Surgical Technique, Jun. 2012.

*Primary Examiner* — Sameh R Boles
(74) *Attorney, Agent, or Firm* — Law Office of Alan W. Cannon

(57) ABSTRACT

Systems, assemblies, components and methods for correcting alignment of one or more vertebrae of a spine are provided. A first elongate derotator member includes a first elongate element having a first proximal end portion and a first distal end portion. The first distal end portion is releasably engageable with a first implant implanted in one of the vertebrae. A second elongate derotator member comprising a second elongate element is releasably engageable with a second implant implanted in the same vertebra. A transverse member is engageable with the first and second elongate elements. A first channel extends axially through the first elongate element and a second channel extends axially through the second elongate element such that a proximal end portion of the first implant can be accessed from a proximal end portion of the first elongate element by inserting a tool through the first channel and a proximal end portion of the second implant can be accessed from a proximal end portion of the second elongate element by inserting the tool or another tool through the second channel.

17 Claims, 12 Drawing Sheets

Related U.S. Application Data continuation of application No. 14/875,414, filed on Oct. 5, 2015, now Pat. No. 9,861,393, which is a division of application No. 13/777,998, filed on Feb. 26, 2013, now Pat. No. 9,179,957, which is a continuation-in-part of application No. 13/717,599, filed on Dec. 17, 2012, now Pat. No. 9,155,581, which is a continuation-in-part of application No. 13/570,374, filed on Aug. 9, 2012, now Pat. No. 9,572,598.

(51) Int. Cl.
  *A61B 17/88* (2006.01)
  *A61B 90/00* (2016.01)
  *A61B 17/68* (2006.01)

(52) U.S. Cl.
  CPC ........ *A61B 17/708* (2013.01); *A61B 17/7034* (2013.01); *A61B 17/7035* (2013.01); *A61B 17/7037* (2013.01); *A61B 17/7038* (2013.01); *A61B 17/7049* (2013.01); *A61B 17/7079* (2013.01); *A61B 17/7085* (2013.01); *A61B 17/7091* (2013.01); *A61B 17/8605* (2013.01); *A61B 17/88* (2013.01); *A61B 90/03* (2016.02); *A61B 2017/681* (2013.01); *A61B 2090/037* (2016.02)

(56) References Cited

U.S. PATENT DOCUMENTS

| | | |
|---|---|---|
| 5,020,519 A | 6/1991 | Hays et al. |
| 5,102,412 A | 4/1992 | Rogozinski |
| 5,176,679 A | 1/1993 | Lin |
| 5,181,917 A | 1/1993 | Rogozinski |
| 5,196,013 A | 3/1993 | Harms et al. |
| 5,207,678 A | 5/1993 | Harms et al. |
| 5,219,349 A | 6/1993 | Krag et al. |
| 5,261,907 A | 11/1993 | Vihnaud et al. |
| 5,281,223 A | 1/1994 | Ray |
| 5,360,431 A | 11/1994 | Puno et al. |
| 5,425,732 A | 6/1995 | Ulrich |
| 5,437,669 A | 8/1995 | Yuan et al. |
| 5,474,555 A | 12/1995 | Puno et al. |
| 5,478,340 A | 12/1995 | Kluger |
| 5,531,747 A | 7/1996 | Ray |
| 5,545,166 A | 8/1996 | Howland |
| 5,591,165 A | 1/1997 | Jackson |
| 5,624,442 A | 4/1997 | Mellinger et al. |
| 5,632,744 A | 5/1997 | Campbell, Jr. |
| 5,649,926 A | 7/1997 | Howland |
| 5,672,175 A | 9/1997 | Martin |
| 5,702,392 A | 12/1997 | Wu et al. |
| 5,702,457 A | 12/1997 | Walch et al. |
| 5,704,937 A | 1/1998 | Martin |
| 5,707,371 A | 1/1998 | Metz-Stavenhagen |
| 5,733,284 A | 3/1998 | Martin |
| 5,797,910 A | 8/1998 | Martin |
| 5,814,046 A | 9/1998 | Hopf |
| 6,015,409 A | 1/2000 | Jackson |
| 6,090,113 A | 7/2000 | Le Couedic et al. |
| 6,171,311 B1 | 1/2001 | Richelsoph |
| 6,251,112 B1 | 6/2001 | Jackson |
| RE37,665 E | 4/2002 | Ralph et al. |
| 6,402,753 B1 | 6/2002 | Cole et al. |
| 6,458,131 B1 | 10/2002 | Ray |
| 6,511,484 B2 | 1/2003 | Torode et al. |
| 6,565,568 B1 | 5/2003 | Rogozinski |
| 6,605,088 B1 | 8/2003 | St. Onge et al. |
| 6,648,888 B1 | 11/2003 | Shluzas |
| 6,726,692 B2 | 4/2004 | Bett |
| 6,749,613 B1 | 6/2004 | Conchy et al. |
| 6,755,828 B2 | 6/2004 | Shevtsov et al. |
| 6,916,319 B2 | 7/2005 | Munting |
| 6,945,933 B2 | 9/2005 | Branch et al. |
| 7,004,947 B2 | 2/2006 | Shluzas et al. |
| 7,090,679 B2 | 8/2006 | Saint-Martin et al. |
| 7,144,396 B2 | 12/2006 | Shluzas |
| 7,306,606 B2 | 12/2007 | Sasing |
| 7,338,491 B2 | 3/2008 | Baker et al. |
| 7,371,239 B2 | 5/2008 | Dec et al. |
| 7,465,306 B2 | 12/2008 | Pond, Jr. et al. |
| 7,655,008 B2 | 2/2010 | Lenke et al. |
| 7,682,377 B2 | 3/2010 | Konieczynski et al. |
| 7,722,652 B2 | 5/2010 | Justis et al. |
| 7,727,261 B2 | 6/2010 | Barker et al. |
| 7,766,915 B2 | 8/2010 | Jackson |
| 7,785,354 B2 | 8/2010 | Biedermann et al. |
| 7,794,464 B2 | 9/2010 | Bridwell et al. |
| 7,867,258 B2 | 1/2011 | Drewry et al. |
| 7,879,075 B2 | 2/2011 | Shluzas |
| 7,896,902 B2 | 3/2011 | Jeon et al. |
| 7,901,435 B2 | 3/2011 | Slivka et al. |
| 7,942,909 B2 | 5/2011 | Hammill, Sr. et al. |
| 7,951,173 B2 | 5/2011 | Hammill, Sr. et al. |
| 7,955,363 B2 | 6/2011 | Richelsoph |
| 7,967,849 B2 | 6/2011 | Carson et al. |
| 8,021,397 B2 | 9/2011 | Farris et al. |
| 8,057,519 B2 | 11/2011 | Justis et al. |
| 8,075,603 B2 | 12/2011 | Hammill, Sr. et al. |
| 8,080,036 B2 | 12/2011 | Shim et al. |
| 8,088,152 B2 | 1/2012 | Schumacher |
| 8,128,667 B2 | 3/2012 | Jackson |
| 8,137,387 B2 | 3/2012 | Garamszegi |
| 8,162,989 B2 | 4/2012 | Khalili |
| 8,167,910 B2 | 5/2012 | Nilsson |
| 8,221,474 B2 | 7/2012 | Bridwell et al. |
| 9,179,957 B2 | 11/2015 | Ibrahim et al. |
| 9,480,500 B2 | 11/2016 | Ibrahim et al. |
| 9,668,776 B2 | 6/2017 | Ibrahim et al. |
| 9,861,393 B2 | 1/2018 | Ibrahim et al. |
| 10,028,773 B2 | 7/2018 | Ibrahim et al. |
| 10,213,232 B2 | 2/2019 | Ibrahim et al. |
| 2003/0144665 A1 | 7/2003 | Munting |
| 2003/0225408 A1 | 12/2003 | Nichols et al. |
| 2004/0034350 A1 | 2/2004 | Onge et al. |
| 2004/0172022 A1 | 9/2004 | Landry et al. |
| 2004/0249378 A1 | 12/2004 | Saint Martin et al. |
| 2005/0033291 A1 | 2/2005 | Ebara |
| 2005/0033299 A1 | 2/2005 | Shluzas |
| 2005/0149036 A1 | 7/2005 | Varieur et al. |
| 2005/0149053 A1 | 7/2005 | Varieur et al. |
| 2005/0159757 A1 | 7/2005 | Shluzas et al. |
| 2005/0171540 A1 | 8/2005 | Lim et al. |
| 2005/0182400 A1 | 8/2005 | White |
| 2005/0245928 A1 | 11/2005 | Colleran et al. |
| 2006/0106380 A1 | 5/2006 | Colleran et al. |
| 2006/0149236 A1 | 7/2006 | Barry |
| 2006/0195092 A1 | 8/2006 | Barry |
| 2006/0200132 A1* | 9/2006 | Chao ................. A61B 17/7077 606/86 A |
| 2006/0235390 A1 | 10/2006 | Zhang et al. |
| 2006/0271050 A1 | 11/2006 | Piza Vallespir |
| 2007/0049933 A1 | 3/2007 | Ahn et al. |
| 2007/0093846 A1 | 4/2007 | Frigg et al. |
| 2007/0161989 A1 | 7/2007 | Heinz et al. |
| 2007/0173827 A1 | 7/2007 | Morrison et al. |
| 2007/0213715 A1 | 9/2007 | Bridwell et al. |
| 2007/0213716 A1 | 9/2007 | Lenke et al. |
| 2008/0234757 A1 | 9/2008 | Jacofsky et al. |
| 2009/0105769 A1 | 4/2009 | Rock et al. |
| 2009/0105771 A1 | 4/2009 | Lei et al. |
| 2009/0204159 A1 | 8/2009 | Justis et al. |
| 2009/0228053 A1 | 9/2009 | Kolb et al. |
| 2010/0094343 A1 | 4/2010 | Pham et al. |
| 2010/0145394 A1 | 6/2010 | Harvey et al. |
| 2010/0204735 A1 | 8/2010 | Gephart et al. |
| 2010/0305621 A1 | 12/2010 | Wang et al. |
| 2010/0324610 A1 | 12/2010 | Bridwell et al. |
| 2011/0172714 A1 | 7/2011 | Boachie-Adjei et al. |
| 2011/0178558 A1 | 7/2011 | Barry |

\* cited by examiner

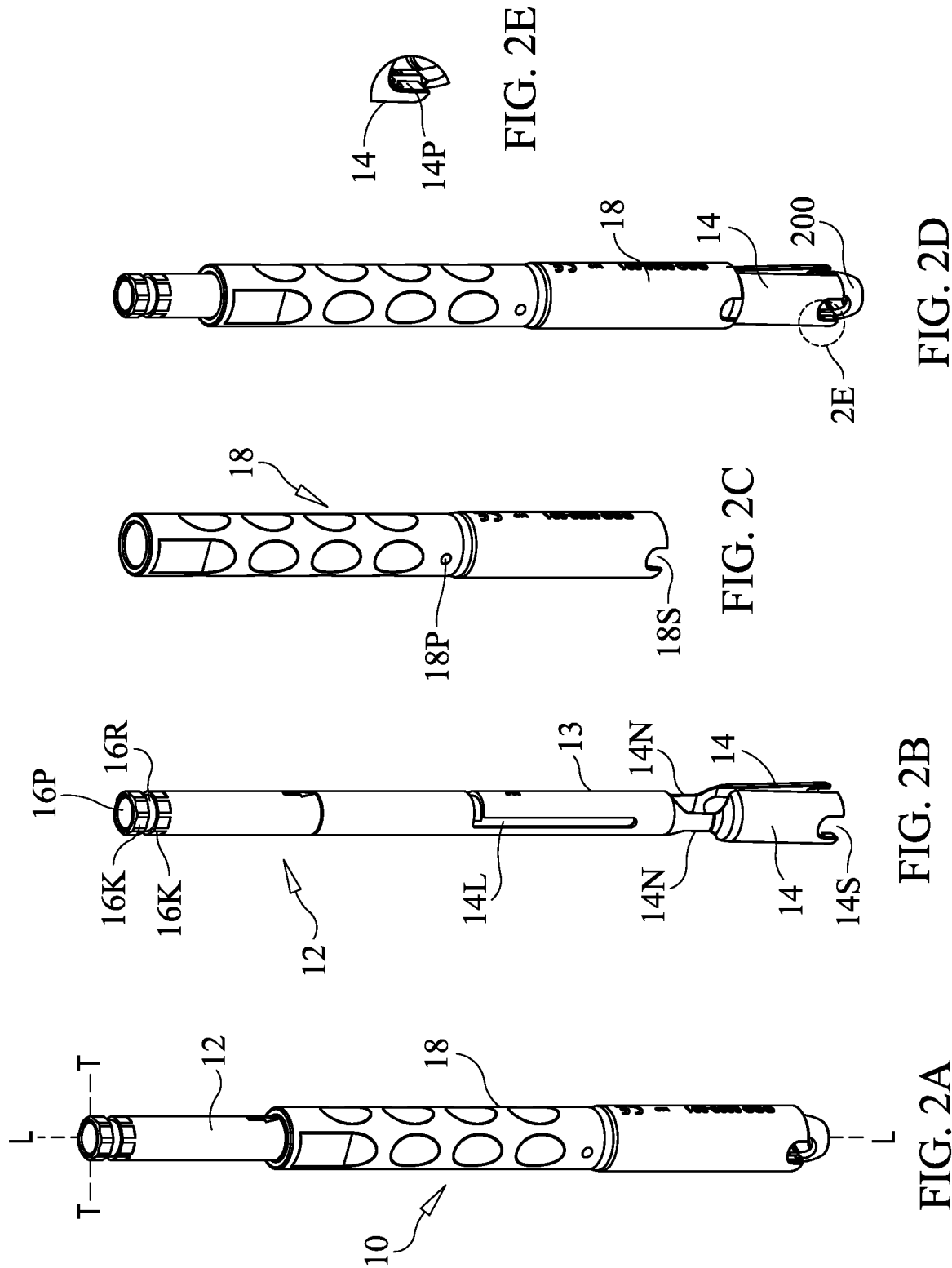

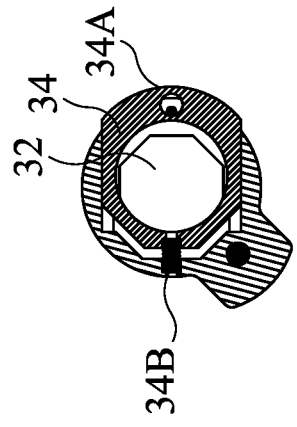
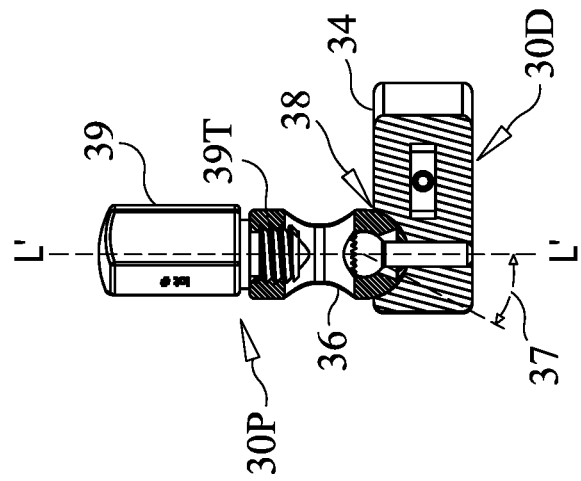
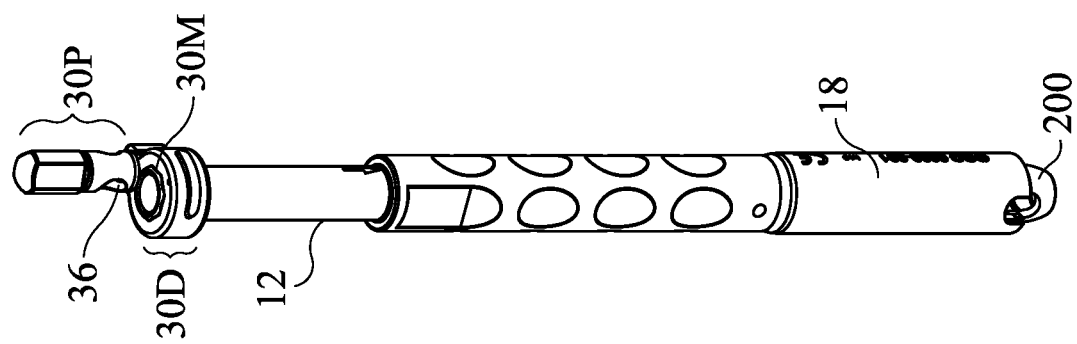
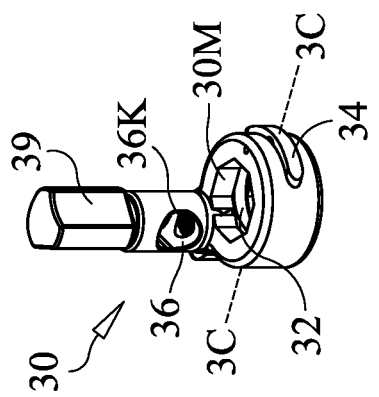

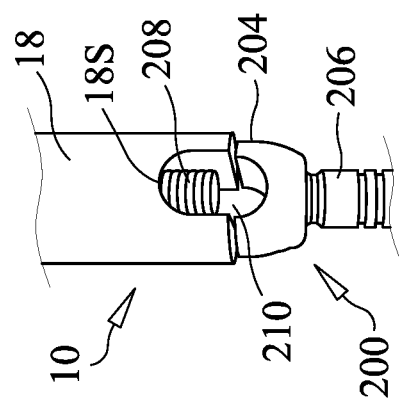
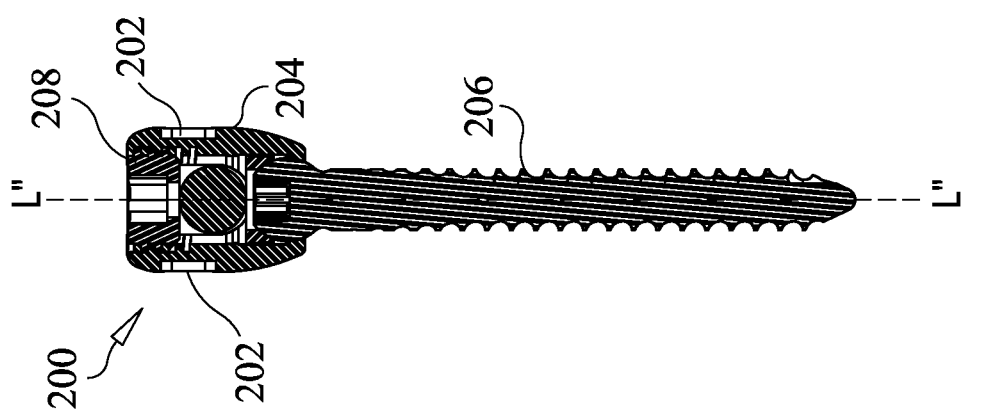
FIG. 5
FIG. 4

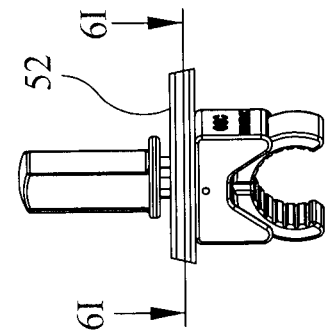
FIG. 6E
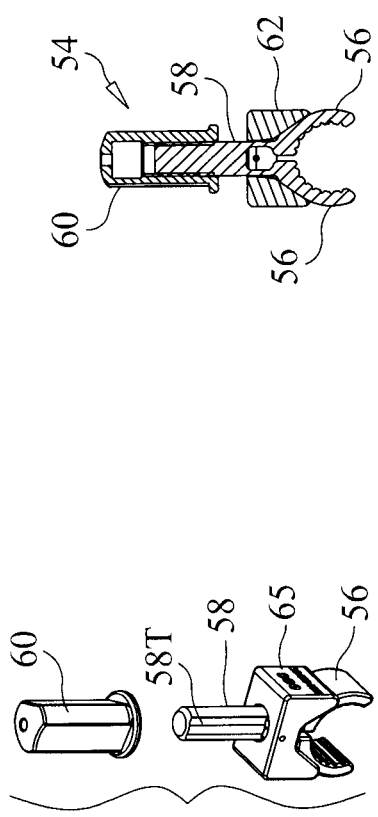
FIG. 6F
FIG. 6G
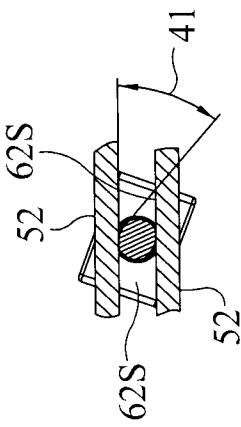
FIG. 6H
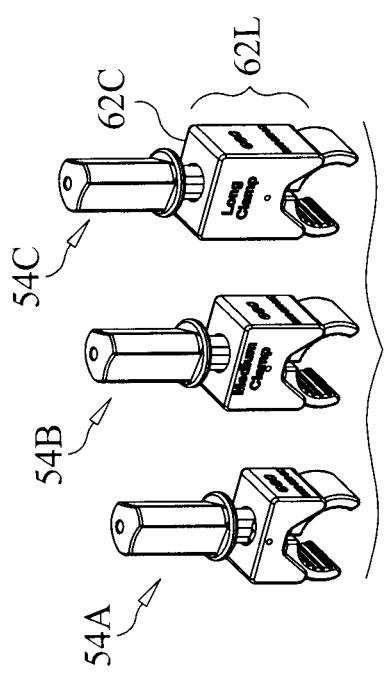
FIG. 6I

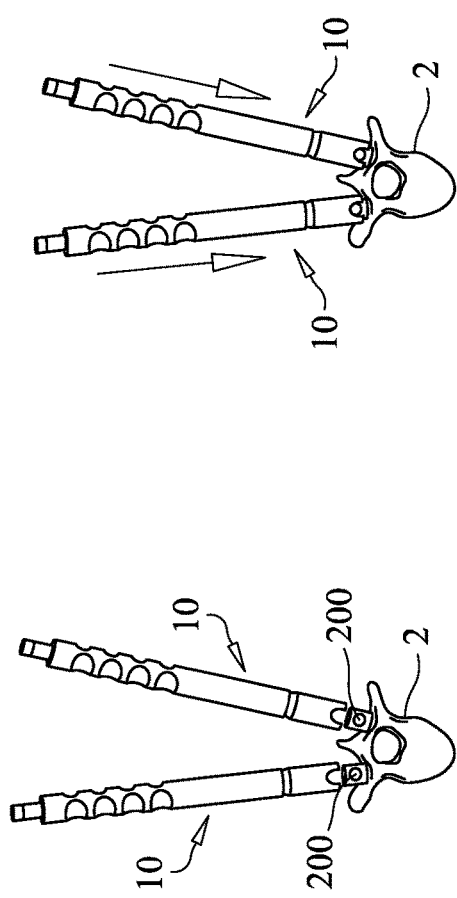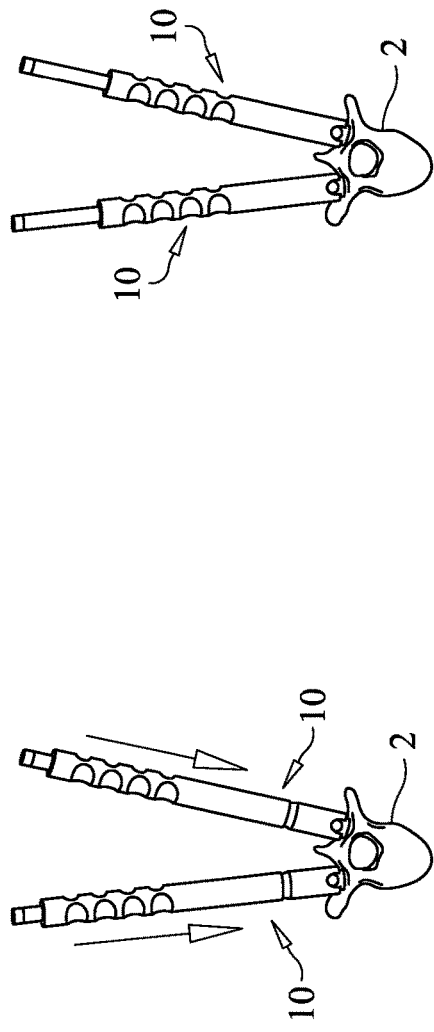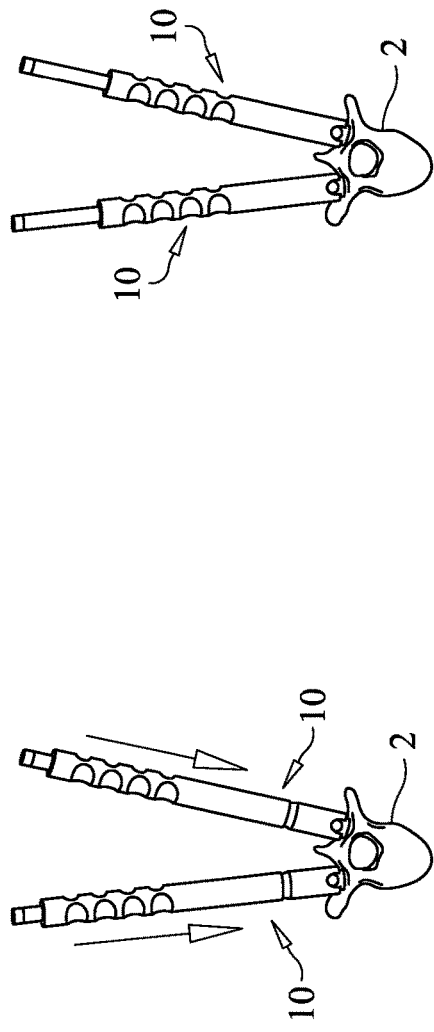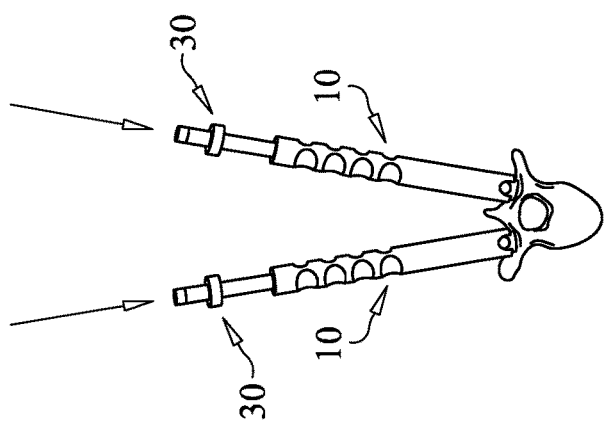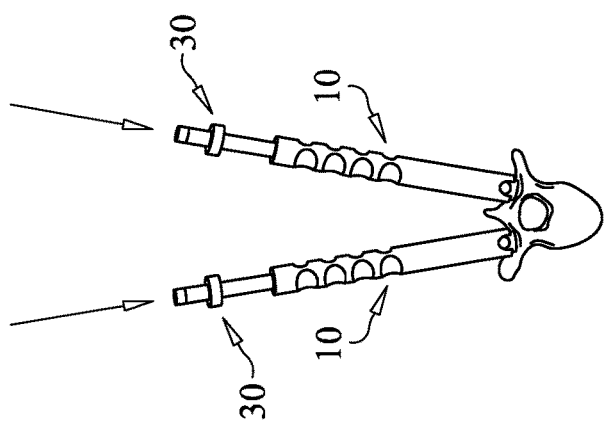
FIG. 10C
FIG. 10E
FIG. 10B
FIG. 10D
FIG. 10A

SYSTEMS, ASSEMBLIES AND METHODS FOR SPINAL DEROTATION

CROSS-REFERENCE

This application is continuation of co-pending application Ser. No. 15/822,047, filed Nov. 24, 2017, which is a continuation of application Ser. No. 14/875,414, filed Oct. 5, 2015, now U.S. Pat. No. 9,861,393, issued Jan. 9, 2018, which is a division of application Ser. No. 13/777,998, filed Feb. 26, 2013, now U.S. Pat. No. 9,179,957, issued Nov. 10, 2015, which is a continuation-in-part of application Ser. No. 13/717,599 filed Dec. 17, 2012, now U.S. Pat. No. 9,155,581, issued Oct. 13, 2015, which is a continuation-in-part of application Ser. No. 13/570,374, filed Aug. 9, 2012, now U.S. Pat. No. 9,572,598, issued Feb. 21, 2017, which applications and patents are hereby incorporated herein, in their entireties, by reference thereto, and to which applications we claim priority under 35 USC § 120. This application also references application Ser. No. 13/717,565 filed Dec. 17, 2012, which application is hereby incorporated herein, it its entirety, by reference thereto.

FIELD OF THE INVENTION

The present invention relates to the field of orthopedic surgery, in particular to devices, systems and assemblies for stabilizing and/or fixing bones and/or joints in a patient. More particularly, the present invention relates to instruments, assemblies and methods for correcting spinal alignment.

BACKGROUND OF THE INVENTION

The fixation and/or stabilization of bones and/or bone fragments is/are commonly required by orthopedic surgeons to treat injuries such as fractures or disease. To accomplish this, the bones/bone fragments can be joined by a rod, plate or the like, which is fixed to the bones/bone fragments via fasteners such as screws, pins or the like. The connection by the rod(s), plate(s) or the like maintains the bones/bone fragments in a desired orientation and/or at desired spacings, positions, etc.

In spinal surgery, it is often necessary to secure various implants to the vertebrae and interconnect the vertebrae by attaching one or more rods or plates to the implants. Due to the complex curvature of the spine, as well as irregularities of the same that often need to be treated, it is often difficult to align a rod or plate with all of the implants/fasteners fixed to the various vertebrae to be connected via the rod or plate. In some surgeries, it is necessary to span multiple vertebrae of the spine with rods that provide stabilizing forces to the vertebrae to help maintain the desired orientations of the vertebrae to maintain a desired curvature in the spine. In these instances, repositioning of multiple vertebrae is often required, often by repositioning relative to multiple planes, in order to achieve the desired alignment of the vertebrae and correct the curvature of the spine/deformity being treated.

There is a need for instruments, assemblies and procedures to facilitate such complex realignment procedures. There is a need for instrument, assemblies and methods that not only can perform these complex procedures, but which also facilitate the ability to more readily attach the instruments when the vertebrae are out of alignment and where it would be otherwise difficult or impossible, using conventional instrumentation to interconnect instrumentation being used because of extreme malalignment of the vertebrae being treated.

SUMMARY OF THE INVENTION

According to one aspect of the present invention, a system for correcting alignment of one or more vertebrae of a spine is provided, including: the first elongate derotator member comprising a first elongate element having a first proximal end portion and a first distal end portion, the first distal end portion being releasably engageable with a first implant implanted in one of the vertebrae; a second elongate derotator member comprising a second elongate element having a second proximal end portion and a second distal end portion, said second distal end portion being releasably engageable with a second implant implanted in the one of the vertebrae; and a transverse member engageable with the first and second proximal end portions of the first and second elongate elements; wherein a first channel extends axially through the first elongate element and a second channel extends axially through the second elongate element such that a proximal end portion of the first implant can be accessed from a proximal end portion of the first elongate element by inserting a tool through the first channel when the first elongate derotator member is engaged with the first implant and a proximal end portion of the second implant can be accessed from a proximal end portion of the second elongate element by inserting the tool or another tool through the second channel when the second elongate derotator member is engaged with the second implant.

In at least one embodiment, the proximal end portion of the first implant can be accessed from the proximal end portion of the first elongate element by inserting a tool through the first channel when the transverse member is engaged with the first proximal end portion of the first elongate element and wherein the proximal end portion of the second implant can be accessed from the proximal end portion of the second elongate element by inserting the tool or another tool through the second channel when the transverse member is engaged with the proximal end portion of the second elongate element.

In at least one embodiment, the first elongate derotator member further comprises a third elongate element slidable over the first elongate element, wherein the third elongate element is distally slidable relative to the first elongate element to lock engagement of the first distal end portion with the first implant; and wherein the second elongate derotator member further comprises a fourth elongate element slidable over the second elongate element, wherein the fourth elongate element is distally slidable relative to the second elongate element to lock engagement of the second distal end portion with the second implant.

In at least one embodiment, the system further includes the first and second implants.

In at least one embodiment, the system further includes: a first linking member configured to engage the transverse member with the first proximal end portion of the first elongate element; and a second linking member configured to engage the transverse member with the second proximal end portion of the second elongate element; wherein the first linking member is releasably engageable with the first proximal end portion of the first elongate element and the second linking member is releasably engageable with the second proximal end portion of the second elongate element.

In at least one embodiment, the first linking member comprises a distal end portion having a first longitudinal axis aligned with a longitudinal axis of the first elongate member when the first linking member is engaged with the first elongate member, and a proximal end portion configured to engage with the transverse member, the proximal end portion of the first linking member having a second longitudinal axis offset from the first longitudinal axis; and the second linking member comprises a distal end portion having a third longitudinal axis aligned with a longitudinal axis of the second elongate member when the second linking member is engaged with the second elongate member, and a proximal end portion configured to engage with the transverse member, the proximal end portion of the second linking member having a fourth longitudinal axis offset from the third longitudinal axis.

In at least one embodiment, the system further includes a first ball joint interconnecting the proximal end portion of the first linking member with the distal end portion of the first linking member; and a second ball joint interconnecting the proximal end portion of the second linking member with the distal end portion of the second linking member.

In at least one embodiment, the system further includes: a third elongate derotator member comprising a third elongate element having a third proximal end portion and a third distal end portion, the third distal end portion being releasably engageable with a third implant implanted in a second one of the vertebrae; a fourth elongate derotator member comprising a fourth elongate element having a fourth proximal end portion and a fourth distal end portion, the fourth distal end portion being releasably engageable with a fourth implant implanted in the second one of the vertebrae; and a second transverse member engageable with the third and fourth proximal end portions of the third and fourth elongate elements; wherein a third channel extends axially through the third elongate element and a fourth channel extends axially through the fourth elongate element such that a proximal end portion of the third implant can be accessed from a proximal end portion of the third elongate element by inserting the tool or another tool through the third channel when the third elongate derotator member is engaged with the third implant and a proximal end portion of the fourth implant can be accessed from a proximal end portion of the fourth elongate element by inserting the tool or another tool through the fourth channel when the fourth elongate derotator member is engaged with the fourth implant.

In at least one embodiment, the system further includes an interlevel linking assembly extending between and engaged with the first elongate derotator member and the third elongate derotator member.

In another aspect of the present invention, a system for correcting alignment of one or more vertebrae of a spine includes: a first elongate derotator member comprising a first elongate element having a first central longitudinal axis, a first proximal end portion and a first distal end portion, the first distal end portion being releasably engageable with a first implant implanted in one of the vertebrae; a second elongate derotator member comprising a second elongate element having a second central longitudinal axis, a second proximal end portion and a second distal end portion, the second distal end portion being releasably engageable with a second implant implanted in the one of the vertebrae; and a transverse member engageable with the first and second proximal end portions of the first and second elongate elements; wherein the first central longitudinal axis is substantially aligned with a longitudinal axis of a head of the first implant when the first elongate derotator member is engaged with the first implant, and wherein the second central longitudinal axis is substantially aligned with a longitudinal axis of a head of the second implant when the second elongate derotator member is engaged with the second implant.

In at least one embodiment, the first elongate derotator member further comprises a third elongate element slidable over the first elongate element, wherein the third elongate element is distally slidable relative to the first elongate element to lock engagement of the first distal end portion with the first implant; and the second elongate derotator member further comprises a fourth elongate element slidable over the second elongate element, wherein the fourth elongate element is distally slidable relative to the second elongate element to lock engagement of the second distal end portion with the second implant.

In at least one embodiment, the system further includes the first and second implants.

In at least one embodiment, the system further includes: a first linking member configured to engage the transverse member with the first proximal end portion of the first elongate element; and a second linking member configured to engage the transverse member with the second proximal end portion of the second elongate element; wherein the first linking member is releasably engageable with the first proximal end portion of the first elongate element and the second linking member is releasably engageable with the second proximal end portion of the second elongate element.

In at least one embodiment, the first linking member is attachable to and detachable from the first elongate element without the use of tools, and the second linking member is attachable to and detachable from the second elongate element without the use of tools.

In at least one embodiment, the first linking member comprises a first releasable engagement member movable between an engaged position and a disengaged position and vice versa, and when the first linking member is mounted on the first elongate element and the first releasable engagement member is in the engaged position, the first releasable engagement member engages a first mating engagement element of the first elongate element, thereby preventing dismounting of the first linking member from the first elongate element; and the second linking member comprises a second releasable engagement member movable between an engaged position and a disengaged position and vice versa, and when the second linking member is mounted on the second elongate element and the second releasable engagement member is in the engaged position, the second releasable engagement member engages a second mating engagement element of the second elongate element, thereby preventing dismounting of the second linking member from the second elongate element.

In at least one embodiment, the first and second releasable engagement members are respectively prebiased to the engaged position.

In at least one embodiment, the first linking member comprises a first distal end portion having a first longitudinal axis aligned with a longitudinal axis of the first elongate member when the first linking member is engaged with the first elongate member, and a first proximal end portion configured to engage with the transverse member, the proximal end portion of the first linking member having a second longitudinal axis offset from the first longitudinal axis; and the second linking member comprises a second distal end portion having a third longitudinal axis aligned with a longitudinal axis of the second elongate member when the second linking member is engaged with the second elongate member, and a second proximal end portion configured to engage with the transverse member, the second proximal end portion of the second linking member having a fourth longitudinal axis offset from the third longitudinal axis.

In at least one embodiment, the system further includes: a first ball joint interconnecting the first proximal end portion of the first linking member with the first distal end portion of the first linking member; and a second ball joint interconnecting the second proximal end portion of the second linking member with the second distal end portion of the second linking member.

In at least one embodiment, the first linking member comprises a first distal end portion, a first proximal end portion and a first ball joint interconnecting the first distal end portion and the first proximal end portion, wherein the first proximal end portion is configured to releasably engage with the transverse member and the first distal end portion is configured to releasably engage with the first elongate element; and the second linking member comprises a second distal end portion, a second proximal end portion and a second ball joint interconnecting the second distal end portion and the second proximal end portion, wherein the second proximal end portion is configured to releasably engage with the transverse member and the second distal end portion is configured to releasably engage with the second elongate element.

In at least one embodiment, the system further includes: a third elongate derotator member comprising a third elongate element having a third proximal end portion and a third distal end portion, the third distal end portion being releasably engageable with a third implant implanted in a second one of the vertebrae; a fourth elongate derotator member comprising a fourth elongate element having a fourth proximal end portion and a fourth distal end portion, the fourth distal end portion being releasably engageable with a fourth implant implanted in the second one of the vertebrae; and a second transverse member engageable with the third and fourth proximal end portions of the third and fourth elongate elements.

In at least one embodiment, the system further includes an interlevel linking assembly extending between and engaged with the first elongate derotator member and the third elongate derotator member.

In another aspect of the present invention, a system for correcting alignment of one or more vertebrae of a spine includes: a first elongate derotator member comprising a first elongate element having a first central longitudinal axis, a first proximal end portion and a first distal end portion, the first distal end portion being releasably engageable with a first implant implanted in one of the vertebrae; a first linking member comprising a first proximal end portion and a first distal end portion; a second elongate derotator member comprising a second elongate element having a second central longitudinal axis, a second proximal end portion and a second distal end portion, the second distal end portion being releasably engageable with a second implant implanted in the one of the vertebrae; a second linking member comprising a second proximal end portion and a second distal end portion; and a transverse member engageable with the first and second linking members; wherein the first distal end portion of the first linking member is configured to engage the first proximal end portion of the first elongate derotator member, the first proximal end portion of the first linking member is configured to releasably engage with the transverse member, and the first proximal end portion of the first linking member is articulatable in three dimensions relative to the first distal end portion of the first linking member when the first distal end portion of the first linking member is fixed relative to the first elongate derotator member; and wherein the second distal end portion of the second linking member is configured to engage the second proximal end portion of the second elongate derotator member, the second proximal end portion of the second linking member is configured to releasably engage with the transverse member, and the second proximal end portion of the second linking member is articulatable in three dimensions relative to the second distal end portion of the second linking member when the second distal end portion of the second linking member is fixed relative to the second elongate derotator member.

In at least one embodiment, the first proximal end portion of the first linking member further comprises a first driver actuatable to releasably lock the transverse member in engagement with the first linking member and to releasably lock the first proximal end portion of the first linking member relative to the first distal end portion of the first linking member, thereby preventing articulation of the first proximal end portion of the first linking member relative to the first distal end portion of the first linking member; and the second proximal end portion of the second linking member further comprises a second driver actuatable to releasably lock the transverse member in engagement with the second linking member and to releasably lock the second proximal end portion of the second linking member relative to the second distal end portion of the second linking member, thereby preventing articulation of the second proximal end portion of the second linking member relative to the second distal end portion of the second linking member.

In another aspect of the present invention, a derotator member useful in a system for correcting alignment of one or more vertebrae of a spine includes: a first elongate element having a first proximal end portion and a first distal end portion, the first distal end portion being longitudinally split into at least two split portions configured to releasably engage with an implant implanted in one of the vertebrae; and a second elongate element slidable over the first elongate element, the second elongate element having a second proximal end portion and a second distal end portion; wherein the second distal end portion is slidable over at least part of the split portions thereby preventing the split portions from deforming away from one another; and wherein the distal end portion is slidable away from the split portions to an extent to allow the split portions to deform away from one another.

In at least one embodiment, the distal end portion is hollow, the derotator member further comprising protrusions extending inwardly from the split portions, the protrusions configured to be inserted into female mating features on a head of the implant to engage the implant.

In at least one embodiment, the first elongate element comprises two split portions and each the split portion comprises two protrusions.

In at least one embodiment, the first elongate element is hollow, allowing a tool to be inserted through a proximal opening thereof in the proximal end portion to engage a portion of the implant when the distal end portion is engaged with the implant.

In at least one embodiment, the derotator member further includes a keyed outer surface at the proximal end portion of the first elongate member, the keyed outer surface configured to engage with a mating keyed inner surface of a linking member to prevent rotation of the linking member relative to the first elongate member.

In at least one embodiment, the derotator member further includes a recess in an outer surface of the proximal end portion of the first elongate member, the recess configured to engage with a locking feature of a linking member to prevent detachment of the linking member from the first elongate member when the locking feature is engaged in the recess.

In at least one embodiment, the keyed outer surface allows multiple angular orientations of the linking member relative to a transverse axis of the first elongate member.

In at least one embodiment, the derotator member is provided in combination with a linking member engaged with the first elongate member.

In another aspect of the present invention, a linking member for linking a derotator member to a transverse member in a system useful for correcting alignment of one or more vertebrae of a spine includes: a distal end portion and a proximal end portion; the distal end portion comprising a first opening configured to receive and releasably engage with a proximal end portion of the derotator member; the proximal end portion comprising a second opening configured to receive and releasably engage with the transverse member, wherein the second opening is oriented transverse to an orientation of the first opening; a surface defining the first opening comprising a keyed inner surface configured to maintain an angular orientation of the linking member relative to a transverse axis of the derotator member when the linking member is engaged with the derotator member; a locking element movable from a locked configuration to an unlocked configuration and vice versa, wherein, when in the locked configuration, the locking element extends into the first opening; and wherein the proximal end portion is articulatable relative to the distal end portion in three dimensions.

In at least one embodiment, the linking member further includes an unlocking actuator actuatable to move the locking element from the locked configuration to the unlocked configuration.

In at least one embodiment, the locking element is biased to the locked configuration, so that when the actuator is not being actuated, the locking element is in the locked configuration.

In at least one embodiment, the keyed inner surface is multifaceted and permits selection from multiple different angular orientations of the linking member relative to the transverse axis of the derotator member, wherein the linking member is maintained in a selected angular orientation once engaged with the derotator member at the selected angular orientation.

In at least one embodiment, the linking member further includes a driver actuatable to releasably lock the transverse member in engagement with the linking member after insertion of the transverse member into the second opening, and to releasably lock the first end portion of the linking member relative to the distal end portion of the linking member, thereby preventing articulation of the proximal end portion relative to the distal end portion.

In at least one embodiment, the linking member is provided in combination with a handle having first and second ends, wherein the second end of the handle is configured to mate with the driver and, upon mating with the driver, the handle is manipulatable to operate the driver.

In at least one embodiment, the linking member further includes protrusions extending into the second opening, the protrusion configured to increase friction with the transverse member upon receipt and engagement of the transverse member by the proximal end portion.

In at least one embodiment, the linking member further includes a ball joint interlinking the proximal end portion and the distal end portion and facilitating articulation of the proximal end portion relative to the distal end portion.

In at least one embodiment, the linking member is provided in combination with a transverse member and a derotator member, wherein the distal end portion of the linking member is engaged with and fixed relative to the derotator member and the transverse member is received in the proximal end portion, while the proximal end portion and the transverse member are free to articulate in three dimensions relative to the distal end portion.

In at least one embodiment, the linking member is provided in combination with a transverse member and a derotator member, wherein the distal end portion of the linking member is engaged with and fixed relative to the derotator member and the proximal end portion is fixed relative to the transverse member, wherein the transverse member is and the proximal end portion are fixed relative to the distal end portion.

In at least one embodiment, the linking member is provided in combination with a handle having first and second ends, wherein the second end of the handle is configured to mate with a driver configured to drive locking of the transverse member and the proximal end portion relative to the distal end portion and, upon mating with the driver, the handle is manipulatable to operate the driver; and wherein the first end of the handle is configured to be inserted into a proximal opening of the derotator member and, upon insertion into the proximal opening, the handle is manipulatable to drive movement of the derotator member and transverse member.

In another aspect of the present invention, an interlevel linking assembly for linking at least two derotator members on one side of a spine in a system useful for correcting alignment of one or more vertebrae of the spine includes: an elongate interlink member having a length sufficient to span the locations of all of the derotator members to be linked; and a plurality of interlink clamps configured to securely engage the derotator members, each the interlink clamp comprising: clamp jaws configured to releasably engage the derotator member; a shaft extending from the clamp jaws; and a driver actuatable on an end of the shaft extending away from the clamp jaws to actuate the clamp jaws to clamp down on the derotator member; wherein the shaft has sufficient length to extend through an opening in the elongate interlink member and engage the driver on one side of the elongate interlink member while the clamp jaws are positioned on an opposite side of the elongate interlink member.

In at least one embodiment, the interlink clamps are configured to snap fit onto the respective derotator members, after which further clamping force is applicable by actuation of the drivers.

In at least one embodiment, the interlevel linking assembly further includes a base adjacent the clamp jaws, wherein the driver cooperates with the base to drive clamping action of the clamp jaws.

In at least one embodiment, the base is selectable from a plurality of bases each having a different length, and wherein different length bases are selectable to compensate for varying distances between the elongate interlink member and the derotator members.

In at least one embodiment, the elongate interlink member comprises a unitary plate.

In at least one embodiment, the unitary plate comprises a slot extending longitudinally therein, the slot having a length sufficient to span the locations of all of the derotator members to be linked.

In at least one embodiment, the interlink clamps are slidable in the slot, prior to fixation of the interlink clamps.

In at least one embodiment, the interlink clamps are rotatable in the slot, within a controlled range of rotation, prior to fixation of the interlink clamps.

In at least one embodiment, the elongate interlink member comprises a plurality of linked plates, the linked plates being axially rotatable relative to one another, within a controlled range of rotation.

In at least one embodiment, at least one of the linked plates comprises a slot extending longitudinally therein, and wherein one of the interlink clamps is slidable in each slot, prior to fixation thereof.

In at least one embodiment, the interlevel linking assembly is fixedly clamped to the plurality of derotator members.

In at least one embodiment, the interlevel linking assembly is provided in combination with a second plurality of the derotator members on an opposite side of the spine, interconnected to the plurality of derotator members by respective transverse members.

In another aspect of the present invention, a system for correcting alignment of one or more vertebrae of a spine includes: a plurality of pairs of elongate derotator members, each the member comprising a elongate element having a longitudinal axis, a proximal end portion and a distal end portion, the distal end portion being releasably engageable with an implant implanted in one of the vertebrae in a manner that the longitudinal axis is substantially aligned with a longitudinal axis of the implant; wherein a first of each the pair is located on a first side of the spine and engageable with an implant implanted on a first side of the vertebra and a second of each pair is respectively located on a second side of the spine and engageable with an implant on the same vertebra on the second side of the spine, and wherein each the derotator member on the first side of the spine is adapted to be engaged to a different vertebra from the vertebra that each of the other derotator members on the first side of the spine is adapted to be engaged to; a plurality of interlink members with one of the interlink members attached to each of the derotator members, respectively; a plurality of transverse members with one of the transverse members attached to each the pair of derotator members through the interlink members, respectively, wherein the transverse members connect to the interlink members at locations offset from the longitudinal axes of the elongate elements; and at least one handle attached to one of a proximal opening of one of the elongate elements or a proximal end portion of one of the interlink members.

In at least one embodiment, the system further includes an interlevel linking assembly attached directly to a plurality of the derotator members on one of the first and second sides of the spine.

In another aspect of the present invention, a method of assembling a system for correcting alignment of a spinal column of a patient includes: engaging a distal end portion of respective first and second derotation members to respective ones of first and second implants implanted in a vertebra of the spinal column on opposite sides of the spinal column; engaging a first interlink member with a proximal end portion of the first derotation member and engaging a second interlink member with a proximal end portion of the second derotation member; engaging a transverse member with proximal end portions of the first and second interlink members, at locations offset from longitudinal axes of the first and second derotation members, respectively; and manipulating at least one member of the system to align the spinal column.

In at least one embodiment, the method further includes engaging at least one handle with at least one location selected from a proximal end portion of one of the derotation members and a proximal end portion of one of the interlink members, such that the handle is substantially aligned with the longitudinal axis of the respective derotation member or proximal end portion of the interlink member; and wherein the manipulating at least one member includes manipulating the at least one handle.

In at least one embodiment, the method further includes implanting the first and second implants prior to the engaging a distal end portion of respective first and second derotation members to respective ones of first and second implants implanted in a vertebra of the spinal column on opposite sides of the spinal column.

In at least one embodiment, the method further includes engaging first and second elongate stabilization elements to the first and second implants, respectively, after the manipulating to provide post-operative stabilization.

In at least one embodiment, the method further includes: engaging a distal end portion of respective third and fourth derotation members to respective ones of third and fourth implants implanted in a second vertebra of the spinal column on opposite sides of the spinal column; engaging a third interlink member with a proximal end portion of the third derotation member and engaging a fourth interlink member with a proximal end portion of the fourth derotation member; and engaging a second transverse member with proximal end portions of the third and fourth interlink members, at locations offset from longitudinal axes of the third and fourth derotation members, respectively.

In at least one embodiment, the method further includes engaging an interlevel linking assembly to adjacent ones of the derotation members on one side of the spinal column.

In at least one embodiment, the method further includes inserting a tool through a longitudinally extending opening in one of the derotation members and performing an operation on the implant that the one of the derotation members is engaged with, from a location proximal of a proximal end the one of the derotation members.

In at least one embodiment, the operation causes a head of the implant to establish a selectable degree of cold welding with a stabilization member received by the implant.

In at least one embodiment, the operation causes a selectable degree of cold welding between a head and a shaft of the implant.

In at least one embodiment the selectable amount of cold welding by the implant with the stabilization member and the selectable amount of cold welding between the head and the shaft of the implant occur during the same operation.

In at least one embodiment, the operation fixes a stabilization member received by the implant, relative to the implant. the engagement of the distal portion comprises pressing the derotator member against the implant to deform a distal opening of the derotator member outwardly and snap fitting the distal portion to the implant.

In at least one embodiment, the method further includes sliding a sleeve distally over the distal portion after the snap fitting to prevent outward deformation of the distal opening.

In at least one embodiment, the engagement of the distal portion comprises engaging inwardly extending protrusions at the distal portion in recesses in the implant.

In at least one embodiment, the method further includes sliding a sleeve distally over the distal portion after engaging the protrusions in the recesses to prevent escape of the protrusions from the recesses.

In at least one embodiment, the proximal end portions of the interlink members are three-dimensionally adjustable relative to the respective derotator members that the interlink members are engaged to, the method comprising three-dimensionally adjusting at least one of the proximal end portions to align with the transverse member for engagement therewith.

In at least one embodiment, the method further includes locking the proximal end portions relative to the respective derotator members, after engaging the transverse member, to prevent articulation of the proximal end portion and the transverse member relative to the derotator member.

In at least one embodiment, the method further includes axially rotating a portion of the interlevel linking assembly relative to another portion of the interlevel linking assembly to better conform to variances in orientations of the derotator members.

These and other features of the present invention will become apparent upon reading the detailed description of the systems, assemblies, components and methods below.

BRIEF DESCRIPTION OF THE DRAWINGS

FIG. 2A is an isolated, plan view of one of the derotator members shown in FIG. 1.

FIG. 2B is an isolated view of an inner elongate element of the derotator member of FIG. 2A.

FIG. 2C is an isolated view of an outer element that is slidably receivable over the element shown I FIG. 2B.

FIG. 2D is a view of the derotator member of FIG. 2A in an unlocked configuration.

FIG. 2E is a detailed view of the portion of FIG. 2D indicated within circle 2E.

FIG. 3A is an isolated, perspective view of a linking member, according to an embodiment of the present invention.

FIG. 3B shows the linking member of FIG. 3A engaged with the derotator member of FIG. 2A.

FIG. 3C is a cross sectional view of FIG. 3A taken along line 3C-3C.

FIG. 3D is a partial longitudinal sectional view of the linking member of FIG. 3A.

FIG. 4 is a longitudinal sectional view of an implant according to an embodiment of the present invention.

FIG. 5 is a partial view showing locking of a derotator member to an implant according to an embodiment of the present invention.

FIG. 6E is an exploded view of a clamp shown in FIG. 6A.

FIG. 6F is a longitudinal sectional view of a clamp shown in FIG. 6A.

FIG. 6G illustrates clamps of varying lengths according to an embodiment of the present invention.

FIG. 6H is a perspective view of a clamp loosely engaged in an (partial view of) an elongate link member according to an embodiment of the present invention.

FIG. 6I is a cross-sectional view of FIG. 6H taken along line 6I-6I.

FIGS. 10A-10I illustrate a method of assembling the assembly of FIG. 1 to establish derotator triangulation, according to an embodiment of the present invention.

DETAILED DESCRIPTION OF THE INVENTION

Figure 1:
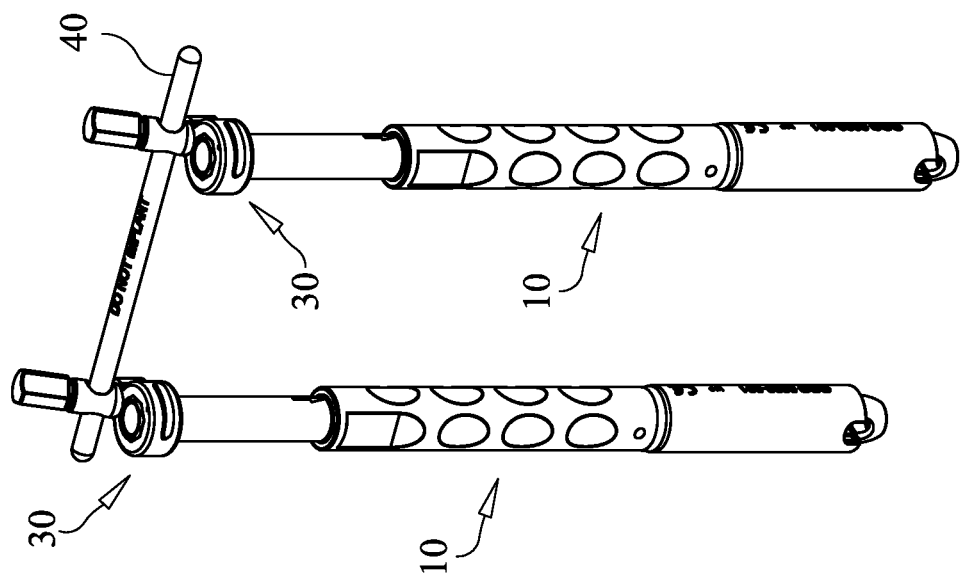
FIG. 1 shows a pair of elongate derotator members linked or engaged with a transverse member by use of linking members according to an embodiment of the present invention.

Before the present instruments, assemblies and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a member" includes a plurality of such members and reference to "the handle" includes reference to one or more handles and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Spinal derotation instrumentation is provided to carry out one or more derotation maneuvers on one or more vertebrae of a patient's spine to correct or improve the orientation of the one or more vertebrae to more closely achieve the normal curvature of the spine. For each of at least one vertebra, a pair of derotation posts are respectively attached to a pair of spinal implants implanted in the vertebra on opposite sides of the vertebra. For each pair of derotation posts connected, a linking member is installed to connect the pair. One or more handles installed on and extending from the derotation posts can then be grasped and used to apply torque to the posts to reposition the vertebra. Posts connected to multiple vertebrae can be linked together and rotated in unison. Alternatively, vertebrae can be independently rotated. Still further, groups of posts on multiple vertebrae can be linked, with still one or more vertebrae having posts attached thereto remaining independent for independent rotation thereof.

Referring now to FIG. 1, a pair of elongate derotator members 10 are shown linked or engaged with a transverse member 40 by use of linking members 30 according to an embodiment of the present invention. FIG. 2A is an isolated, plan view of one of the derotator members 10 shown in FIG. 1. Derotator member 10 includes an inner elongate element 12, as shown in isolation in FIG. 2B. Inner elongated element 12 is typically formed as a rigid tube with split portions 14 being formed at a distal end thereof and forming the distal end portion of the element 12. Necked or otherwise narrowed portions 14N interconnect the split portions 14 with the integral tubular portion 13 of element 12. This provides split portions 14 with resilient flexibility so that they can deform away from one another and then spring back to the resting configuration shown in FIG. 2B, as will be described in greater detail below. Protrusions 14P extend inwardly from distal end portions of split portions 14. Protrusions 14P (see the detail view of FIG. 2E) are configured to be inserted into female mating features on a head of an implant to engage the implant, as described in more detail below. Although two split portions 14 as shown are preferred, the invention is not so limited, as two, three or even more split portions could be provided to function in a same or similar manner. Likewise, it is preferred that four protrusions 14P, two on each split portion are provided, although more or fewer could be used.

Element 12 is hollow along its interior length and includes a proximal end opening 16P that permits a tool to be inserted through the element 12 from opening 16P to extend to the distal end portion of the element and perform an operation on an implant (such as a pedicle screw or other implant) engaged by the split portions 14. The proximal end portion of element 12 includes a keyed outer surface 16K configured to engage and mate with a mating keyed inner surface 30M (see FIG. 3A) of linking member 30 to prevent rotation of the linking member 30 relative to the elongate member 12/derotator member 10. As shown, keyed surface 16K is a multifaceted, polygonal configuration, although other polygonal as well as other multifaceted configurations could be substituted. It is preferred that the keyed surface 16K and mating surface 30M are configured so that linking member 30 can be engaged with elongate member 12 in more than one orientation, where the different orientations are achieved by rotating the linking member about the longitudinal axis L-L relative to the elongate member. Thus, the keyed outer surface allows multiple angular orientations of linking member 30 relative to a transverse axis T-T of the elongate member 12/derotator member 10. In each different selectable orientational position, the linking member mating surface 30M mates with key surface 16K when linking member 30 is mounted on the proximal end portion of element 12 and thereafter prevents rotation of the linking member 30 relative to element 12 about axis L-L. A recessed locking feature 16R such as a recess, groove or other equivalent structure is provided to cooperate with a locking feature of linking member 30 to prevent the linking member 30 from moving axially relative to element 12 along axis L-L after engagement of the linking member with the element 12, and thus preventing inadvertent detachment of the linking member from elongate member 12 when the locking feature of the linking member 30 is engaged in recessed locking feature 16R.

FIG. 2C is an isolated view of an outer element 18 that is slidably received over element 12 of derotator member 10. Element 18 is preferably a rigid tube having a length less than the length of element 12 so that it can be slid between an engaged or locked position (illustrated in FIG. 2A) and a disengaged or unlocked position (illustrated in FIG. 2D). In the disengaged position shown in FIG. 2D, all or a major portion of the split portions 14 extend distal of the distal end of element 18. This allows split portions 14 to deform away from one another as the distal end of element 12/portions 14 contact the proximal end of an implant 200 to be engaged, as illustrated in FIG. 2D, the distal end(s) of element 12/portions 14 may be beveled inwardly to facilitate driving the portions away from each other as they are driven against the distal end edge surfaces of the implant 200. As the derotator member 10 is driven further distally relative to the implant 200, the protrusions 14P pass over the external surface of a distal portion of the implant 200 until they reach the level of female mating features 202 (see FIG. 4) of the implant 200. The portions 14 resiliently move toward one another (driven by the spring force developed during the deformation away from one another) thereby engaging protrusions 14P in mating features 202. At this stage, element/sleeve 18 is next slid distally relative to element 12, from a position such as illustrated in FIG. 2A to a position shown in FIG. 2D, where the distal end portion of element 18 surrounds substantially all of the split portions 14, thereby preventing the ability of split portions 14 to deform away from one another, and ensuring that protrusions 14P remain engaged in mating features 202, thereby locking derotator member 10 to implant 200. Alternatively, split portions 14 can be configured such that, in their unbiased positions, they extend slightly apart from one another, such that the split portions 14 and protrusions 14P can pass over the distal end portion of the implant without deforming. In this case, as element 18 is slid from the unlocked position to the locked position, it compresses the split portions, driving them toward one another and driving the protrusions 14P into the mating recesses 202.

Both element 12 and element 18 have slots or recesses (14S, 18S respectively) that are configured to allow a stabilization element (such as a rod, bar, plate or the like) received by implant 200 to also extend through the elements 12,18 of derotator member 10. Element 12 includes a slot 14L that is engaged by a pin 18P that extends inwardly into element 18. Slot 14L functions as a track along which pin 18P slides, thereby ensuring that recesses 14S, 18S align in the locked position, and also prevents element 18 from sliding off of element 12 if the assembly is inverted prior to attaching linking member 30 to element 12. In at least one embodiment, slot 14L is a Z-shaped or L-shaped slot formed in element 12 that is engaged by pin 18P.

Turning now to FIG. 3A, an isolated, perspective view of linking member 30 is shown, according to an embodiment of the present invention. FIG. 3B illustrates the linking member 20 of FIG. 3A engaged with the derotator member 10 shown in FIG. 2A. Linking member 30 includes a proximal end portion 30P and a distal end portion 30D. Distal end portion 30D includes an opening 32 configured and dimensioned to receive a proximal end portion of element 12 as described above. The mating keyed inner surface 30M prevents rotation of the linking member 30 relative to the elongate member 12/derotator member 10 once engaged therewith as shown in FIG. 3B. Prior to that, the keying configuration shown allows selection from a plurality of different rotational orientations of the linking member relative to element 12 as already described above.

A locking element 34 is movable from a locked configuration (illustrated in the cross-sectional view of FIG. 3C) to an unlocked configuration, and vice versa. In the embodiment shown, a portion of the locking element extends out from the external surface of the distal end portion 30D surrounding it, and can be pressed inwardly to move from the locked configuration to the unlocked configuration In FIG. 3C, it is shown that locking element 34 is biased to the locked configuration by biasing member 34B. When linking member 30 is mounted over the proximal end portion of element 12, the actuation surface 34A of locking element 34 can be pressed inwardly so as to move the locking element 34 (move to the left in FIG. 3C) to align its opening with the opening 32. However, pressing the actuation surface 34A inwardly during mounting is not necessary, as the locking element 34 will self-align with the opening during mounting. However, once locked into recess 16R, it is necessary to press 34A to unlock the locking element 34. Thus, if pressed during mounting, the actuation surface 34A can then be released and, as the locking element 34 is moved distally past the distal most portion of keyed surface 16K and comes into alignment with recess 16R, biasing element 34B drives a portion of the locking element 34 into recess 16R, thereby snapping it into place and axially locking linking member 30 relative to element 12. This same process occurs automatically if the surface 34A is not pressed and released during mounting. Linking member 30 can be removed from element 12 by again depressing the actuation surface 34A to unlock the locking element 34 and linking member can be readily slid off the end of element 12.

Proximal end portion 30P includes an opening 36 configured and dimension to receive and engage transverse member 40. Spikes, protrusions, knurling or other surface roughness 36K can be provided on the inner surface defining opening 36 so as to enhance friction between the inner surface and the transverse member 40 upon engagement therewith. Proximal end portion 30P is articulatable relative to the distal end portion in three dimensions, when in an unlocked configuration. In the embodiment of FIGS. 3A-3D, proximal end portion 30P is connected to distal end portion 30D by a ball and socket joint arrangement 38, see FIG. 3D. This arrangement, in the unlocked configuration, allows rotation of proximal end portion by 360 degrees about the longitudinal axis L'-L' of linking member 30 and allows tilting up to a maximum angle 37 of about 40 degrees, typically the maximum angle is about 20 degrees, and in at least one embodiment, the maximum angle may be about 15 degrees. This angulation, from zero degrees up to the maximum angle 37 can be performed at any rotational position 360 degrees about the axis L'-L'. Thus, in an unlocked configuration, proximal end portion 30P is three-dimensionally articulatable relative to distal end portion 30D.

Proximal end portion 30P further includes a driver 39 that is actuatable to releasably lock the transverse member 40 in engagement with linking member 30 after insertion of the transverse member 40 into opening 36. As shown in the embodiment of FIG. 3D, driver 39 includes a threaded shaft 39T that can be torqued into opening 36 to apply force against transverse member 40 when it is received therein, thereby locking the position of transverse member 40 relative to proximal end portion 30P. At the same time, actuation of the driver 39 as described locks the proximal end portion 30P relative to the distal end portion 30D, as the ball and socket joint is also locked and proximal end portion 30P can no longer articulate relative to distal end portion 39D. Thus, transverse member 40, proximal end portion 30P, distal end portion 30D and derotator member 10 are all rigidly linked at this stage. Additionally, all of these rigidly linked components are also rigidly linked to implant 200. Therefore, any movement of any component 40, 30P, 30D, 10, 200 will cause movement of the vertebra in which the implant 200 is implanted.

FIG. 4 is a longitudinal sectional view of an implant 200 that can be used according to an embodiment of the present invention. In this embodiment, implant 200 is a pedicle screw, which can be a polyaxial, monoaxial or fixed screw. In the case of a polyaxial screw, the head 204 of the implant can angulate relative to the longitudinal axis L"-L" of the implant in the direction/plane of any transverse axis. A monoaxial screw allows the head 204 to angulate relative to L"-L" in only one transverse plane and a fixed screw does not allow angulation of the head 204 relative to the shaft 206. It is noted that this is exemplary only and that the present invention is not limited to any particular type of implant 200 used, or even to use of a pedicle screw, as other types of implants could be used as long as they have the capability of attaching to a vertebra with sufficient attachment force to move and manipulate the vertebra, such as by rotation, without loosening or any other failure, and so long as they are configured to be engaged with and locked to element 12.

FIG. 5 is a partial view illustrating derotator member 10 engaged with implant 200. A portion of set screw 208 is visible as partially extending into the opening 210 formed in the head 204 of implant 200 that is provided to receive a stabilization rod or the like. As noted above, a tool can be inserted through element 12 to drive the set crew 208 so as to lock the stabilization rod relative to the head 204 and/or to loosen it for repositioning. In addition, in cases where polyaxial or monoaxial screws are used, the tool can also be inserted to drive set screw 208 to lock or unlock the articulation capability of head 204 relative to shaft 206.

In order to rigidly link multiple assemblies of the type shown in FIG. 1, thereby rigidly linking multiple levels/vertebra of a spine to as to manipulate in unison, an interlinking assembly can be provided to engage multiple derotator assemblies and rigidly link them. FIG. 6A is a perspective view of an interlevel linking assembly 50 according to an embodiment of the present invention. Interlevel linking assembly 50 includes an elongate interlink member 52 having a length sufficient to span the locations of all of the derotator members 10 to be linked and having sufficient rigidity to transfer forces from one derotator member to all derotator members 10 connected thereto, without any significant deformation or loss of force. In the embodiment shown in FIG. 6A, the assembly 50 is provided to link four derotator members 10. However, the present invention is not limited to this number, as the concepts described here are readily adaptable to assemblies configured to link two, three, or more than four derotator members 10. A plurality of interlink clamps 54 are provided in the assembly 50 and are configured to securely engage the derotator members 10.

Interlink clamp 54 includes clamp jaws 56 configured to releasably engage the derotator member 10; a shaft 58 (see FIG. 6E) extending from the clamp jaws 56; and a driver 60 threadably actuatable on an end of shaft 58 extending away from the clamp jaws 56 to actuate the clamp jaws to clamp down on the element 12 of derotator member 10. The shaft 58 has sufficient length to extend through an opening 52L in the elongate interlink member 52 and engage the driver 60 on one side of elongate interlink member 52 while clamp jaws 56 are positioned on an opposite side of elongate interlink member 52, as illustrated in FIG. 6A. In this regard, shaft 58 can be threaded 58T, for example and driver knob 60 can be provided with mating threads so that driver knob 60 can be torqued against the interlink member 52. As the shaft 58 is drawn into the driver knob 60 by torqueing the knob 60 (with clamp jaws 56 being prevented from rotating about the axis of shaft 58, as having been engaged with element 12) this drives the base portion 62 of the driver assembly (since it is slidable relative to shaft 58) against clamp jaws 56. The concave curvature of the base surface contacting the clamp jaws 56 drives the clamp jaws into compression, causing them to securely and rigidly engage the element 12 of derotator member 10. At the same time, the clamp 54 becomes rigidly fixed relative to interlink member 52. Prior to actuating the driver 60, clamp 54 can slide along opening 52L (typically formed as a longitudinally extending slot) and can rotate relative to the longitudinal axis of shaft 58 over a controlled range of rotation. For example, the controlled range of rotation may have a maximum angle of rotation of up to about ±170 degrees, or a maximum angle of rotation as low as about ±10 degrees. Currently, the preferred maximum angle of controlled rotation is about ±20 degrees, where the angle 41 is measured between the longitudinal axis of the elongate interlink member 52 and the longitudinal axis of the base 62. Thus, the clamp is rotatable in either direction from an angle 41 of zero degrees up to and including the maximum angle of the controlled rotation range. Stops 62S are provided on the base member 62 which contact the interlink member 52 when the maximum angle 41 has been reached. Prior to actuating the driver, the clamp jaws are preferably configured and dimension to form a snap fit over element 12, so that they can be easily initially attached without the need for actuating the clamps.

Figure 6B:
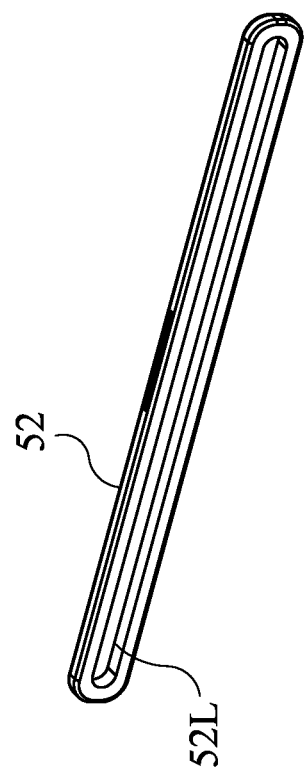
FIG. 6B is a perspective view of the elongate interlink member of FIG. 6A.
Figure 6D:
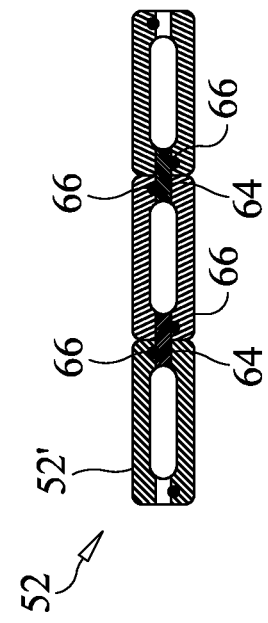
FIG. 6D is a longitudinal sectional view of the elongate link member of FIG. 6C.
Figure 6A:
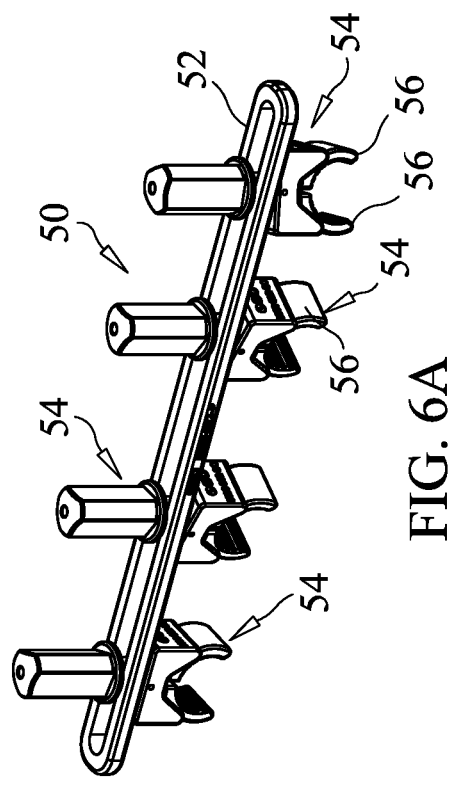
FIG. 6A is a perspective view of an interlevel linking assembly according to an embodiment of the present invention.
Figure 6C:
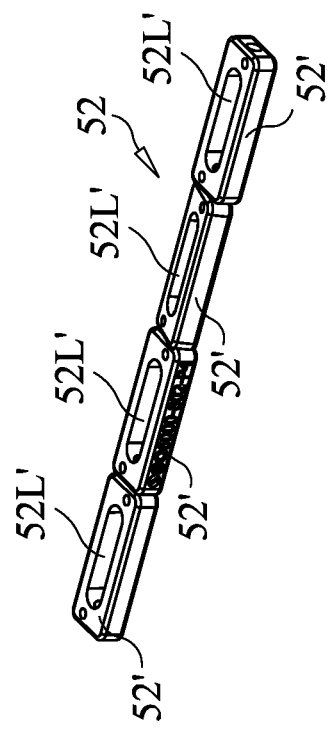
FIG. 6C is a perspective view of an elongate link member according to another embodiment of the present invention.

In FIGS. 6A-6B, the elongate interlink member 52 comprises a rigid, unitary plate and both the plate and the slot 52L have a length sufficient to span all of the derotator members 10 to be linked. In another embodiment, as shown in FIGS. 6C-6D, elongate interlink member 52 comprises a plurality of linked plates 52'. Linked plates 52' are axially rotatable relative to one another, within a controlled range of rotation. Pins 64 are provided to interconnect the plates 52' and plates 52' are rotatable about pins 64. Stops 66 are provided to limit the amount of rotation of one plate 52' relative to an adjacent plate 52' The amount of rotation may be up to about ±30 degrees, typically up to about ±15 degrees. The rotation allowed between links 52' provides an additional degree of freedom that can be useful to facilitate engagement of the assembly 50 with derotator members 10 having varying orientations, as it is often the case that the members will not be parallel due to the misalignment of the vertebrae that they are attached to. Additionally, clamps 54 can slide and rotate about a controlled range of rotation while installed in the links 52', prior to final clamping through actuating the driver 60.

To still further facilitate the attachment of assembly 50 to multiple derotator members 10, clamps 54 of varying lengths may be provided. This can address issues where derotator members 10 are located in orientations resulting in different distances from the plane of the interlink member 52 during attachment. FIG. 6G illustrates three different lengths of clamps 54 (i.e., 54A, 54B and 54C) where 54C has a length greater than 54B and 54B has a length greater than 54A. The variations in length are established by the provision of actuator bases 62 having varying length. In the embodiment of FIG. 6G. the length 62L of base 62C is greater than the length of base 62B and the length of base 62B is greater than the length of base 62A. This also necessitates that the shaft 58 of 54C is longer than the shaft of 54B and the shaft of 54B is longer than the shaft of 54A. FIG. 6F is a longitudinal sectional view of claim 54.

Figure 8B:
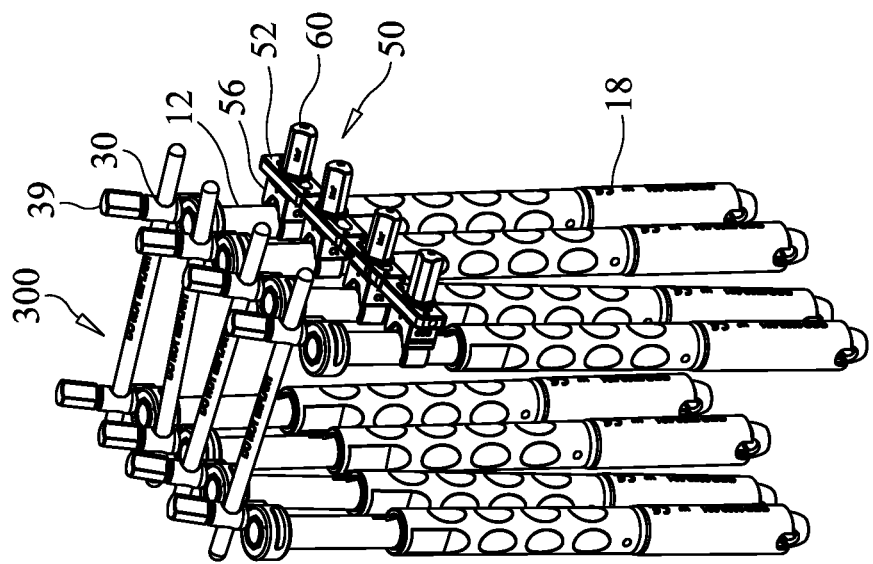
FIG. 8B illustrates the system of FIG. 8A interlinked by an interlevel linking assembly according to an embodiment of the present invention.
Figure 8A:
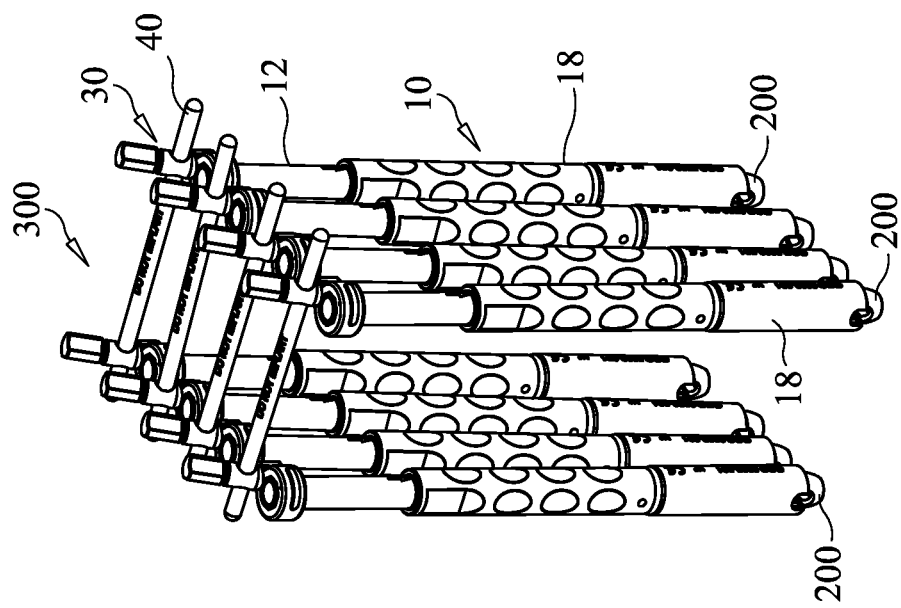
FIG. 8A illustrates a system comprising a plurality of the assemblies shown in FIG. 1, according to an embodiment of the invention.

FIG. 8A illustrates a system including four sets of assemblies of the type shown in FIG. 1, attached to implants 200 implanted in four adjacent vertebrae of a spine (four levels). FIG. 8B shows the system of FIG. 8A after rigidly interlinking the assemblies using interlink assembly 50 in a manner as described above. The system is shown linked by an interlink assembly 50 attached to one side of the system and this is currently the preferred practice. However, the invention is not limited to this embodiment, as the assembly 50 could be attached to the opposite side, or two assemblies 50 (one on each side) could be implemented. Still further, multiple assemblies 50 can be used on one side. For example, one assembly 50 could be engaged to link two adjacent members 10 and a second assembly 50 could be engaged to link two other members 10.

Figure 7:
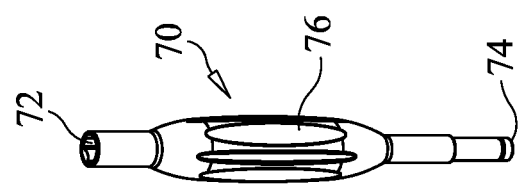
FIG. 7 is a plan view of a handle according to an embodiment of the present invention.

FIG. 7 is a plan view of a handle 70 that can be employed as part of a system according to an embodiment of the present invention. Handle 70 is sufficiently rigid in bending strength to be used to apply moments of force to the assembly 300 without plastically deforming. Handle 70 has sufficient torsional rigidity to allow it to be used as a driver tool A first end of tool 70 comprises a socket 72 configured to mate with at least one of driver 39 and driver 60. Preferably, driver 39 and driver 60 are configured with the same shape and dimensions so that handle 60 can be used to engage and drive both driver 60 and driver 39. Additionally, one or more handles can be engaged to driver 39 and/or driver 60 to apply moments of force to the system 300 to manipulate the spine. However, it is preferred to apply force through the opposite end(s) of the handle(s) 70 by engaging them in the opening(s) 16P as described hereafter. The opposite end 74 of tool 70 is configured and dimensioned to be received in and mate with proximal opening 16P of element 12. Upon such mating, moments of force can be applied to derotator member 10 through handle 70 and element 12. Handle 70 is enlarged in the central portion to form a more comfortable fit to the hand of a user and provide more mechanical advantage when rotating to drive the socket end 72. The central portion may also be knurled, scalloped or otherwise contoured 76 to enhanced friction between the handle and the hand of the user.

Figure 9C:
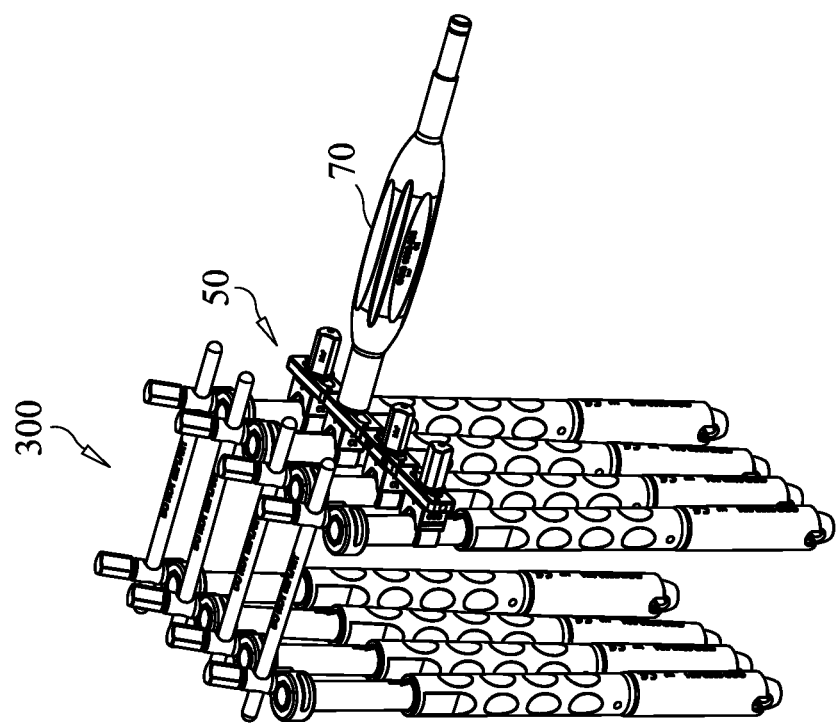
FIGS. 9A-9C illustrate systems having various handle installation arrangements, according to various embodiments of the present invention.
Figure 9B:
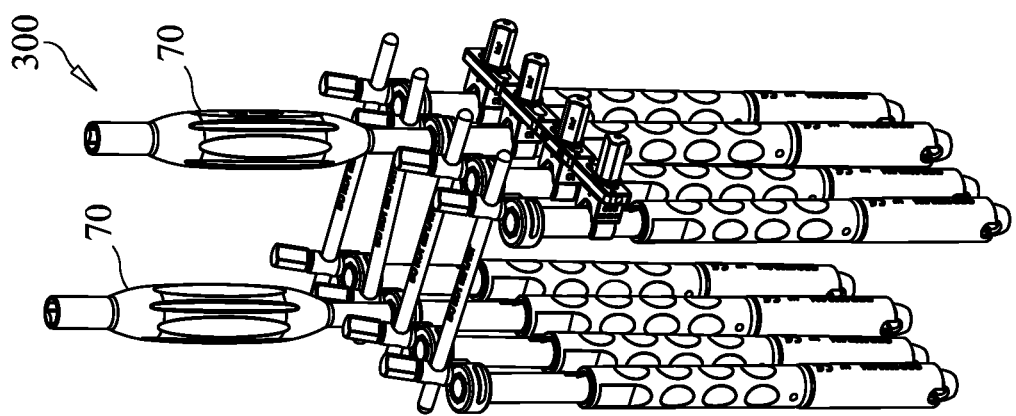
Figure 9A:
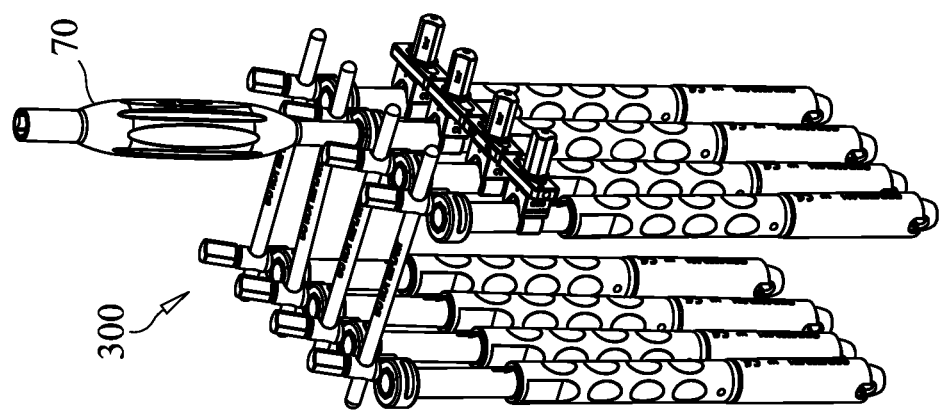

FIG. 9A illustrates system 300 with one handle 70 attached, wherein end 74 is inserted into opening 16P of one of the derotator members. FIG. 9B. illustrates system 300 with two handles 70 attached, wherein end 74 of one handle 70 is inserted into opening 16P of one of the derotator members and end 74 of the other handle is inserted into opening 16P of the other derotator member attached to the same level. FIG. 9C. illustrates system 300 with one handle 70 attached, wherein end 72 is mated over one of the drivers 60 of interlink assembly 50. It is noted that FIGS. 9A-9C are only exemplary, as handles 70 can be engaged with any combination of openings 16P, drivers 30 and drivers 60.

Figure 10G:
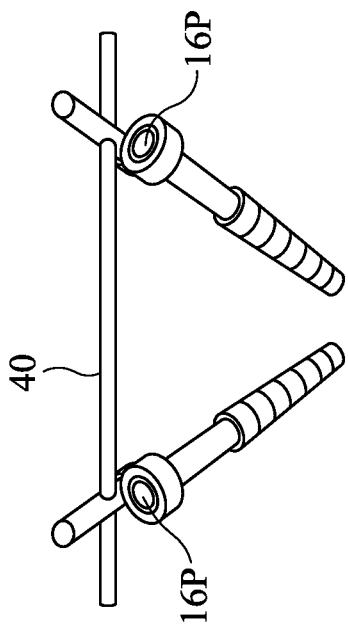
Figure 10G:
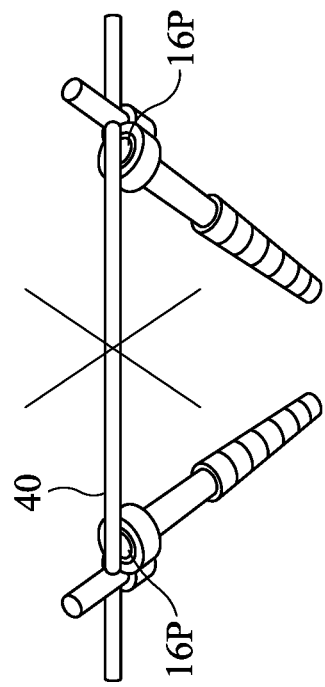

FIGS. 10A-10I illustrate a method of assembling the assembly of FIG. 1 to establish derotator triangulation. Assembling a system 300 can be performed by assembling multiple assemblies in the manner described here and interlinking the assemblies using one or more interlevel linking assemblies as described above. At FIG. 10A, derotator members 10 are advanced toward the heads of the implants 200 having been implanted in vertebra 2. It is noted here that although both sides are being addressed by a single description, the components do not have to be simultaneously assembled on both sides, but can instead, be assembly sequentially. At FIG. 10B, the protrusions 14P have engaged the recesses 202 after forcing the distal ends of the derotator members 10 over the heads of the implants 200. In FIG. 10C, elements 18 (outer sleeves) are slid distally over the split portions 14 to lock the derotator members 10 to the implants 200. FIG. 10D illustrates an optional feature in which a visual indicator 18V (such as a laser-etched arrow or other readily visually identifiable indicator) is provided on element 12 and becomes visible when element 18 has been slid distally sufficient to properly align the distal end of element 18 with the distal end of element 12.

Figure 10F:
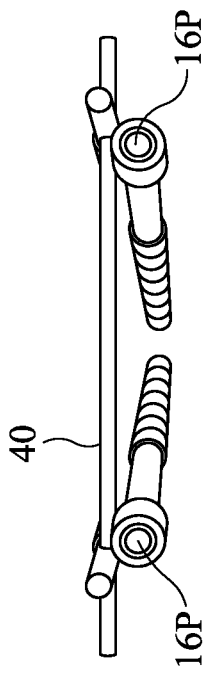
Figure 10F:
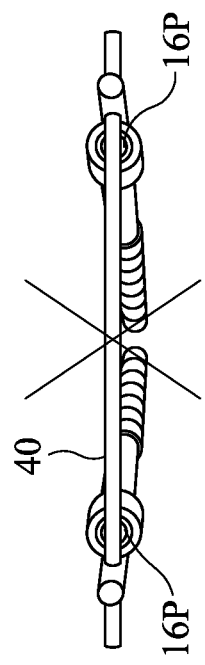

In FIG. 10E the linking members 30 are locked to the derotator members 10. As noted above, in at least one embodiment it is possible to engage the linking member in different rotational orientations relative to the derotator member. The linking members 30 should be oriented such that when transverse member 40 is engaged with the openings 36, the transverse member 40 does not obstruct the openings 16P. This is important as access to openings 16P must be kept open to allow insertions of tools and/or handle 70. FIGS. 10F and 10G are top and side views, respectively, illustrating an assembly in which linking members 30 have been oriented in acceptable positions relative to derotator members 10, where it is shown that openings 16P are readily accessible. In contrast, FIGS. 10F'-10G' are top and side views, respectively, illustrating an assembly in which linking members 30 have been improperly oriented relative to derotator members 10, so that transverse member 40 obstructs the openings 16P making it impossible to access the openings 16P with a tool or handle 70.

Figure 10I:
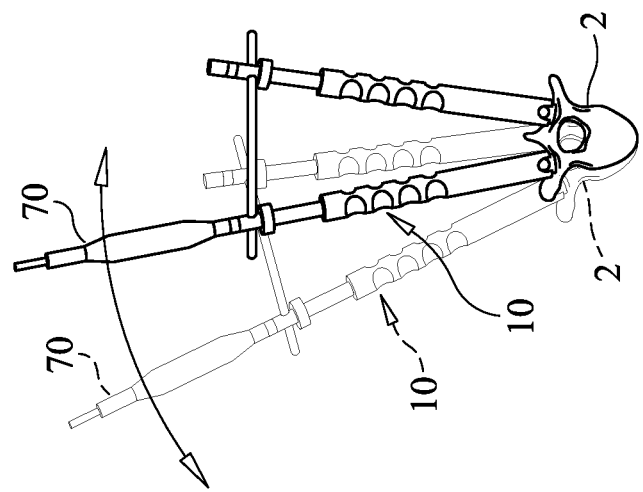
Figure 10H:
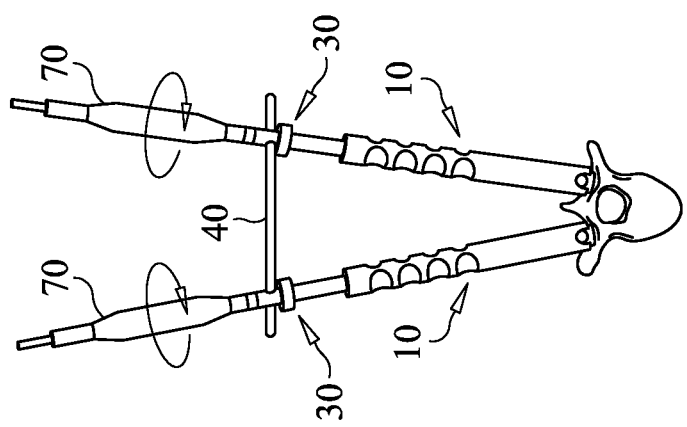

Upon inserting the transverse member, the proximal end portions 30P of linking members 30 can be articulated three dimensionally, such that not only can the proximal end portions 30P and transverse member be tilted toward the head of the patient or the foot of the patient, but they can also be tilted left or right, or in some angular direction in between. In FIG. 10H, after the transverse member 40 has been inserted into linking members 30 and the transverse member 40 and linking member 30 have been articulated relative to derotator members 10 if necessary, one or more handle(s) is/are used to actuate the drivers 70 to lock the transverse member 40 relative to proximal end portion 30P and to lock the proximal end portion 30P relative to distal end portion 30D. In FIG. 10I, the opposite end 74 of tool 70 is inserted into opening 16p of derotator member 10 and force is applied through handle 70 to cause rotation of the assembly and the vertebra as illustrated in phantom.

Figure 11:
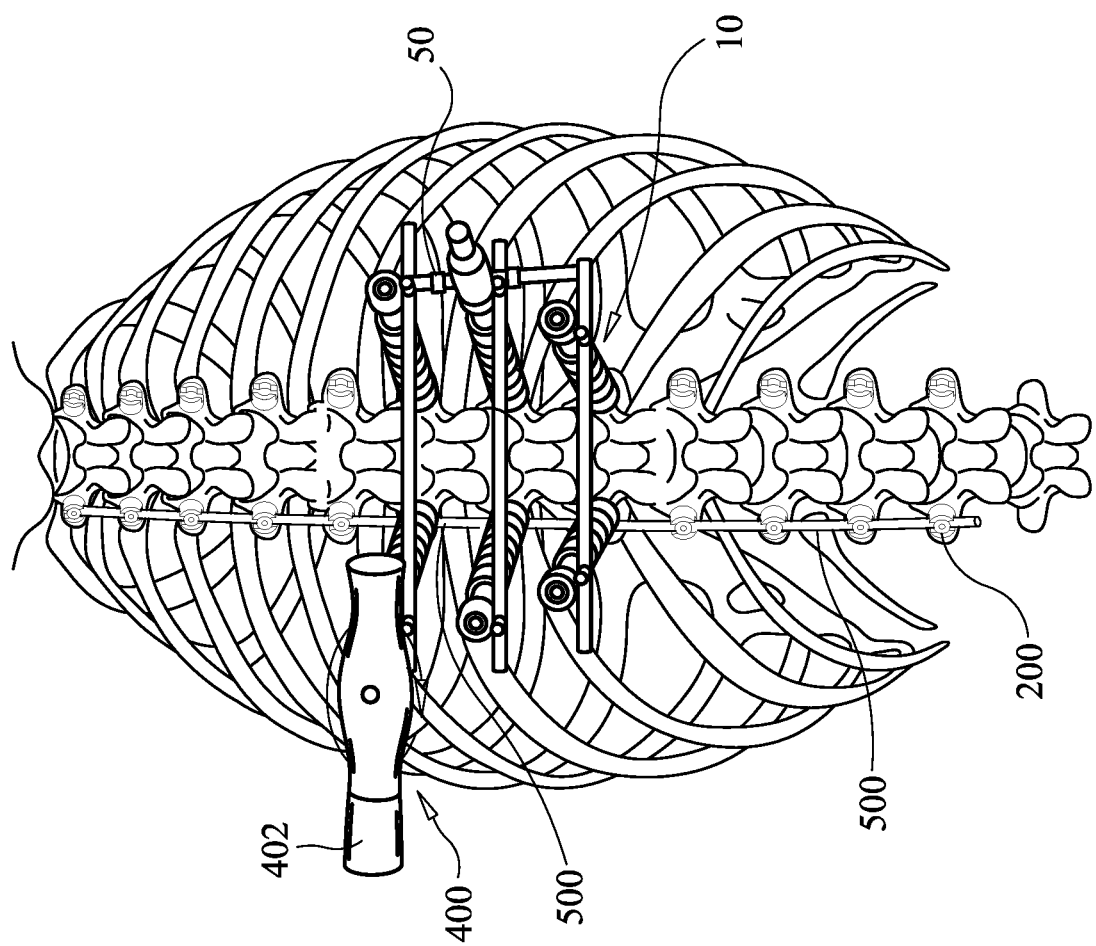
FIG. 11 illustrates insertion of a tool through a proximal end opening of a derotator member to access and implant and perform an operation thereon, according to an embodiment of the present invention.

FIG. 11 illustrates a tool 400 being used to tighten a set screw 208 of implant 200 to lock the orientation of the implant 200 relative to a stabilization rod 500. The working end or distal end portion of the tool 400 has been inserted into opening 16P and through element 12 to interface with the set screw 208 and the set screw is torqued by turning handle 402 of tool 400.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An assembly useful in a system for correcting alignment of one or more vertebrae of a spine, said assembly comprising: a derotator member including a first elongate element and a second elongate element; said first elongate element having a first proximal end portion and a first distal end portion comprising split portions, said first distal end portion being configured to releasably engage with an implant implanted in one of the vertebrae; said first elongate element being hollow along an interior length thereof, with a first proximal end opening configured to permit a tool to be inserted therethrough; said second elongate element configured to slide over said first elongate element, said second elongate element having a second proximal end portion and a second distal end portion; a protrusion extending from one of said first and second elongate elements; and a slot formed in the other of said first and second elements; wherein said protrusion is configured to be received in said slot when said second elongate element is slid over said first elongate element; wherein said first distal end portion comprises first recessed slots configured to allow a stabilization element received by the implant to extend therethrough; wherein said second distal end portion comprises second recessed slots configured to allow the stabilization element received by the implant to extend therethrough; and wherein, upon sliding said second elongate element relative to said first elongate element, said slot functions as a track along which said protrusion slides, thereby ensuring that said second recessed slots align with said first recessed slots.

2. The assembly of claim 1, wherein an end portion of said slot cooperates with said protrusion to prevent said second elongate element from sliding off and separating from said first elongate element when said first and second elongate elements are inverted.

3. The assembly of claim 1, wherein said first proximal end portion comprises a rigid tube and said split portions are configured with resilient flexibility, allowing said split portions to deform away from one another and then resiliently return toward one another.

4. The assembly of claim 1, wherein distal end of said split portions are beveled inwardly to facilitate driving said split portions away from each other when said split portions are driven against the implant.

5. The assembly of claim 1, wherein said split portions diverge from one another in an unbiased configuration, and wherein said second elongate element compresses said split portions toward one another when said second elongate element is slid over said split portions.

6. The assembly of claim 1, wherein said protrusion extends inwardly from an inner wall of said second elongate element and said slot is formed in an outer wall of said first elongate element.

7. The assembly of claim 1, wherein said slot is Z-shaped or L-shaped.

8. The assembly of claim 1, wherein said first elongate element comprises a rigid tube and necked portions interconnecting said split portions with said rigid tube.

9. The assembly of claim 8, wherein said split portions are configured with resilient flexibility, allowing said split portions to deform away from one another and then resiliently return toward one another.

10. The assembly of claim 1, wherein said first proximal end portion comprises a keyed outer surface having a non-circular, cross-sectional shape.

11. The assembly of claim 10, further comprising a linking member configured to link the derotator member to the system, said linking member comprising an opening configured to receive said first proximal end portion, said opening being provided with a keyed inner surface configured to mate with said keyed outer surface.

12. The assembly of claim 11, wherein said keyed inner surface and said keyed outer surface are multifaceted and permit selection from more than two orientations of said linking member relative to said first proximal end portion.

13. An assembly useful in a system for correcting alignment of one or more vertebrae of a spine, said assembly comprising: a derotator member including a first elongate element and a second elongate element; said first elongate element having a first proximal end portion and a first distal end portion comprising split portions, said first distal end portion being configured to releasably engage with an implant implanted in one of the vertebrae, said first distal end portion comprising first recessed slots configured to allow a stabilization element receivable by the implant to extend therethrough; said second elongate element configured to slide over said first elongate element, said second elongate element having a second proximal end portion and a second distal end portion, said second distal end portion comprising second recessed slots configured to allow the stabilization element to extend therethrough; a protrusion extending from one of said first and second elongate elements; and a slot formed in the other of said first and second elements; wherein said protrusion is configured to be received in said slot when said second elongate element is slid over said first elongate element; and wherein said protrusion, when received in said slot, ensures that said second recessed slots remain aligned with said first recessed slots when said second elongate element slides over said first elongate element.

14. The assembly of claim 13, further comprising a linking member configured to link the derotator member to the system, said linking member comprising an opening configured to receive said first proximal end portion.

15. The assembly of claim 14, wherein said first proximal end portion is provided with a keyed outer surface and said opening is provided with a keyed inner surface configured to mate with said keyed outer surface.

16. The assembly of claim 15, wherein said keyed inner surface and said keyed outer surface are multifaceted and permit selection from more than two orientations of said linking member relative to said first proximal end portion.

17. The assembly of claim 14, wherein said linking member comprises a locking element configured to move from a locked configuration to an unlocked configuration and vice versa, and wherein when in said locked configuration, said locking element extends into said opening.

* * * * *